US008486639B2

(12) United States Patent
Morpurgo et al.

(10) Patent No.: US 8,486,639 B2
(45) Date of Patent: Jul. 16, 2013

(54) NANOASSEMBLED COMPLEXES OF NUCLEIC ACIDS, AVIDIN AND POLYMERS, USE AND PREPARATION THEREOF

(75) Inventors: Margherita Morpurgo, Padova (IT); Mauro Pignatto, Marghera (IT); Deborah Teoli, Torreglia (IT)

(73) Assignee: ANANAS Nanotech S.r.L., Padova (IT)

( * ) Notice: Subject to any disclaimer, the term of this patent is extended or adjusted under 35 U.S.C. 154(b) by 451 days.

(21) Appl. No.: 12/667,116

(22) PCT Filed: Jun. 27, 2008

(86) PCT No.: PCT/EP2008/058298
§ 371 (c)(1),
(2), (4) Date: Dec. 29, 2009

(87) PCT Pub. No.: WO2009/003951
PCT Pub. Date: Jan. 8, 2009

(65) Prior Publication Data
US 2010/0197032 A1 Aug. 5, 2010

(30) Foreign Application Priority Data
Jun. 29, 2007 (IT) .............................. PD2007A0223

(51) Int. Cl.
*C12Q 1/68* (2006.01)
*G01N 33/00* (2006.01)

(52) U.S. Cl.
USPC .............................. 435/6.19; 436/93; 436/94

(58) Field of Classification Search
None
See application file for complete search history.

(56) References Cited

PUBLICATIONS

Roberts et al. "Chemistry for peptide and protein PEGylation". 2002. Adv. Drug. Deliv. Rev. vol. 54. pp. 459-476.*
Pignatto et al. "Optimized Avidin Nucleic Acid Nanoassemblies by a Tailored PEGylation Strategy and Their Application as Molecular Amplifiers in Detection", Bioconjugate Chem., 2010, v. 21, pp. 1254-1263.*
Xiong, May P. et al.; "Biotin-triggered release of poly(ethylene glycol)-avidin from biotinylated polyethylenimine enhances in vitro gene expression"; Biaconjugate Chemistry, vol. 18, No. 3, Mar. 22, 2007; pp. 746-753.
Morpurgo, Margherita et al.; "DNA condensation by high-affinity interaction with avidin"; Journal of Molecular Recognition; Nov.-Dec. 2004; vol. 17, No. 6; Nov. 2004; pp. 558-566.
Segura, T. et al.; "Surface-tethered DNA complexes for enhanced gene delivery"; Bioconjugate Chemistry, ACS, Washington, DC; vol. 13, Jan. 1, 2002; pp. 621-629.
Goldenbert, David M., et al; "Antibody Pretargeting Advances Cancer Radiaimunodetection and Radiolmunotherapy"; Journal of Clinical Oncology; vol. 24, No. 5; Feb. 10, 2006; p. 823-834.
Cattel, Luigi et al.; "From Conventional to Stealth Lipoosmes a New Frontier in Cancer Chemotherapy"; Tumori, 89: pp. 237-249; 2003.

(Continued)

*Primary Examiner* — Yelena G Gakh
(74) *Attorney, Agent, or Firm* — Gifford, Krass, Sprinkle, Anderson & Citkowski, P.C.

(57) ABSTRACT

The present invention discloses new nanoassembled complexes consisting of a central nucleus formed by a high-affinity interaction from nucleic acids and avidin, wherein said nucleus is stabilized in aqueous solutions, even saline, and protected from further unspecific unwanted interactions by means of suitable polymeric agents capable to mask totally or partially the nucleus itself. The nanocomplexes obtained have been shown to be stable in aqueous solutions and to have nanoparticle features. In addition, the nano-complexes have shown characteristics useful for use in biotechnological field and in nanomedicine.

28 Claims, 5 Drawing Sheets

PUBLICATIONS

Jeon S.I. et al.; "Protein-Surface Interactions in the Presence of Polyethylene Oxide"; Journal of Colloid and Interface Science, vol. 142, No. 1, Mar. 1, 1991; pp. 149-158.
Jeon, S.I. et al.; "Protein-Surface Interactions in the Presence of Polyethylene Oxide"; Journal of Colloid and Interface Science; vol. 142, No. 1; Mar. 1, 1991; pp. 159-166.
Sofia, Susan J. et al.; "Poly(ethylene oxide) Grafted to Silicon Surfaces: Grafting Density and Protein Adsorption"; Macromolecules 1998, 31, pp. 5059-5070.
Owens, Donald E. III et al,; "Opsonization, biodistribution and pharmacokinetics of polymeric nanoparticles"; International Journal of Pharmaceutics 307 (2006) pp. 93-102.
Green, N.M.; "A Spetrophotometric Assay for Avidin and Biotin Based on Binding of Dyes by Avidin"; Biochem. J. (1965) 94, pp. 23c-24c.
Monfardini, Cristina et al; "A Branched Monomethoxypoly(ethylene glycol) for Protein Mofication"; Bioconjugate Chem. 1995; 6, pp. 62-69.

* cited by examiner

NANOASSEMBLED COMPLEXES OF NUCLEIC ACIDS, AVIDIN AND POLYMERS, USE AND PREPARATION THEREOF

FIELD OF THE INVENTION

The present invention relates to new nanoassembled complexes (also hereinafter known as nanocomplexes or nanoassemblies) and more specifically to nanoassemblies of nucleic acids, avidin and polymers, to their use in the biotechnological field and nanomedicine and to their preparation.

STATE OF THE ART

Avidin is a tetrameric glycoprotein known mainly for its ability to bind to four molecules of biotin with very high affinity ($K_d$~$10^{-15}$ M). From the practical viewpoint, the avidin property of a high and multiple affinity for biotin forms the basis for its use as a molecular instrument in a large number of biotechnological applications (avidin-biotin technology) (Wilchek M and Bayer E A, *Analytical Biochemistry.* 1988, 171: 1-32; Wilchek M and Bayer E A, *Methods Enzymol.* 1990, 184: 14-45). In respect of this property, avidin can serve as a molecular bridge to then stably link together different biological or chemical units, provided that these latter are covalently bound to one molecule of biotin.

The most common applications of avidin-biotin technology are for analytical purposes, more precisely for detection and quantification systems which are usually based on the ability to link an antibody, or any other molecule having high affinity towards the analyte (ligand/antigen), to a marker system (a fluorophore, an enzyme able to emit light/colour, a radionuclide etc.); other applications include surface functionalization with specific chemical/biochemical entities, being a procedure which is often conducted by using the molecular bridge formed from the avidin-biotin complex; another application is for targeting drugs or diagnostic elements, administered by parenteral means, towards specific sites in the body (Goldenberg D M, Sharkey R M, Paganelli G, Barbet J, and Chatal J F, *J. Clin. Oncol.* 2006, 24: 823-834).

One of the main drawbacks of classic avidin-biotin technology is the maximum number of biotins, namely four, that can be joined to a single avidin molecule, which forms the central nucleus of the system. The possibility to have a central nucleus able to bind a greater number of biotin molecules to itself enables the system potentiality to be theoretically increased.

This increased capability can be achieved by joining together several avidin molecules into a single unit (defined herein as a poly-avidin unit). In this regard the literature describes various technological approaches for obtaining said poly-avidin nuclei. The strategies commonly adopted and currently available are based on coating the surfaces of micro- or nano-spheres (consisting of different polymers such as polystyrene or metals, such as gold) with several avidin molecules, or on the chemical "polymerization" of avidin by covalent crosslinking.

Strategies currently available for forming poly-avidin units are hence based either on chemical synthesis processes aimed at the formation of covalent bonds between avidin units, or on non-specific adsorption processes which lead to avidin molecules adhering to the surfaces of polymer or metal nuclei. However, all these systems have certain disadvantages in common. In particular, the poly-avidins thus obtained are always characterized by: a) a certain degree of polydispersivity depending on the method for obtaining them: b) a partial loss of avidin activity. In practical terms, inactivation of avidin translates into a reduced capacity for binding with biotin (and hence with any other biotinylated ligand), whereas polydispersivity translates into products whose properties are statistically defined and are hence not highly defined.

Another common disadvantage of poly-avidins obtained by means of the aforesaid methods is that they cannot be used in certain biomedical environments as the materials used for their assembly (e.g. linkers for chemical polymerization, or polymer or metal central nuclei for non-specific adsorption) are either not of natural origin or are not always biocompatible and therefore potentially toxic. The poly-avidins obtained by these methods can thus present toxicological risks related to the elements comprising them and this limits their applicability in pharmaceutical/diagnostic environments when in vivo contact of the avidin assembly with human or animal tissue is envisaged.

Recently, an additional property specific to avidin has been brought to light, this being its capacity to bind to nucleic acids with high affinity (Morpurgo M, Radu A, Bayer E A, and Wilchek M, *Journal of Molecular Recognition.* 2004, 17: 558-566).

Said binding results from a high affinity interaction which also involves specific regions of the protein but does not involve directly the biotin binding site. Subsequently to this interaction, avidin self-assemblies onto DNA in an organized manner, giving rise to stoichiometrically defined agglomerates. Within them, the nucleic acid is coated by avidin molecules in a stoichiometric ratio of avidin to the nucleic acid base pairs equal to 18±4. These complexes are stable at high dilutions ([DNA]=10 pM) and in the presence of electrolytes in solution.

Given the stability of the interaction under physiological conditions, the aforesaid assemblies can in effect be described as poly-avidins, similar in part to those already mentioned. The assemblies are stable, are composed only of elements of biological and biodegradable origin, and the ability of avidin, contained within them, to bind to biotin remains intact.

However, the practical benefits of these poly-avidin systems as instruments for improving the performance of the classic avidin-biotin system depend on being able to obtain them in the form of reproducible and poorly polydispersed, discrete aggregates of defined colloidal size. From the macroscopic viewpoint the avidin-nucleic acid assemblies are seen to assume various shapes and geometries depending on the conditions in which they are found. For example, by mixing avidin and nucleic acids in a buffered aqueous environment, agglomerates of large size are obtained (>>1 micron), which are highly polydispersed and of undefined geometry and indeed unusable from the practical viewpoint. Conversely, in a salt-free environment and under specific conditions of concentration and ratio of nucleic acids to protein, nanoparticulate structures of toroid or rod shape can be obtained, in which a single nucleic acid molecule is surrounded by several avidin molecules. In this case, the nanoassemblies are poorly polydispersed and their size depends solely on the type and length of the nucleic acid used. However, these latter arrangements, which are already described in the literature (Morpurgo M et al. 2004 ref. cit.), are stable and isolatable in aqueous salt-free solution; in the presence of electrolytes they undergo a rapid process of aggregation subsequent to which polydispersed macro-aggregates are again obtained but actually unusable for practical purposes.

Since any general analytical or biomedical application of the avidin/biotin system comprises biorecognition reactions in saline aqueous environment, the avidin and nucleic acid complexes described above have no practical use because they are unable to exist as discrete and stable entities under the required buffered conditions.

In any event, aggregation is a general problem common to many small sized particles, particularly when they fall within the colloidal range (<1 micron-nanoparticles). Aggregation depends on particle surface characteristics (charge type and density, hydrophobicity, hydrophilicity, etc.) and on the type of medium in which they are suspended (inorganic solvent, aqueous solvent, type of buffer, ionic strength, pH, etc.); various technical solutions can be employed to avoid or slow down aggregation.

Should the suspension medium be an aqueous solution, the most commonly adopted strategy is to use hydrophilic polymers which are covalently bound or adsorbed onto the particle surface so as to partially or completely conceal it from is the surrounding environment. A steric hindrance and an enthalpic gain are thus created which prevent the particles from interacting irreversibly with each other. For example, hydrophilic polymers are used to protect the surface of liposomal nanoparticles (Cattel L, Ceruti M, et al. *Tumori,* 2003, 89:237-249) used as carriers of antitumour drugs to be administered by parenteral means.

The effectiveness of hydrophilic polymers in preventing non-specific interactions between different surfaces (and hence also between nanoparticles) to which they are attached is related to two parameters: a) polymer chain length and b) grafting density (Jeon S I, Lee J H et al. *J. Colloidal and Interface Sci.* 1991, 142: 149-158; Jeon S I and Andrade J D *J. Colloidal and Interface Sci.* 1991, 142: 159-166; Sofia S J, Premnath V et al. *Macromolecules* 1998, 31: 5059-5070). For each system therefore, the same efficacy of aggregation prevention is achievable by varying one, or the other or both the aforesaid parameters.

It should be noted that each system, whether surface or nanoparticulate, is characterised by distinctive properties (chemical, angle of curvature, etc.) and so the efficacy of surface protection must be calibrated each time in order to optimize the effects. As aforecited, various parameters are taken into account during optimization and include type of polymer, its length and attachment density, and not least, the grafting method (Owens D E and Peppas N A *Int. J. Pharm.* 2006, 307: 93-102). Consequently, the results obtained with a determined particle system are not directly transferable to another one and as such, the information already described in the literature is not directly applicable to nanoparticulate systems consisting of avidin and nucleic acids. The surface protection aspect of these systems is therefore described for the first time within the scope of this invention. One aspect of the present invention is to obtain nanoparticles consisting of nucleic acids and avidin which are stable in an aqueous/saline environment.

A further aspect of the present invention is that said stable systems are able to recognize other biotinylated elements, in that they themselves possess pharmacological activity, or are able to recognize third elements (for example a receptor) or are able to generate signals by themselves or in combination with other reagents in solution (for example fluorescence, colour, radioactivity, photons.)

SUMMARY

The nanoassembled complexes provided by the inventors fulfil the aforementioned purposes, as they allow the previously reported drawbacks derived from the known technologies of the art to be overcome.

In particular, the obtained nanoassembled complexes are highly defined from the qualitative and quantitative composition viewpoint and stable even in the presence of electrolytes.

In a first aspect the object of the present invention are nanoassembled complexes comprising a nucleus obtained by means of high affinity interaction between one or more avidin units and one or more nucleic acid molecules, wherein said nucleus is stabilized by a biotinylated surface protecting agent, represented by the general formula (I)

$$NB_nAv_y(B\text{-}X_a\text{-}PA_b)_z \qquad (I)$$

wherein:

NB are the single nucleobases of a single or double stranded nucleic acid;

Av is an avidin unit;

$B\text{-}X_a\text{-}PA_b$ is the biotinylated surface protecting agent in which PA is a polymer unit having at least one or two functionalizable residues of which one binds, by a covalent bond either directly or through a spacer X, to a biotin residue B by means of carboxyl functional group thereof;

n is a number varying from 16 to 10,000,000;

y is an integer equal to or greater than 1 and being relative to n can vary from (0.0001)·n to (0.0454)·n. If a value comprised in the range (0.0001-0.0454)·n is less than (<) 1, then y is equal to (=) 1;

z is an integer equal to or greater than (≧) 1 and being relative to y can vary from (0.02)·y to (4)·y. If a value comprised in the range (0.02-4)·y is less than (≦) 1, then z is equal to (=) 1;

a is a number varying from 0 to 50;

b is a number varying from 1 to 128.

The nanoassembled complexes of the invention are in the form of nanoparticles which are another object of the invention.

A further object of the invention is the use of nanoassembled complexes of formula (I) as means vitro and in vivo diagnostics, in the field of nanomedicine for targeting and concentrating bioactive molecules towards specific sites in the body, in the field of nanotechnology in general for the localization of molecules onto surfaces, and in any application (biomedical and engineering) that requires a co-localization of several chemical or biological functions of varying natures on a central core, being in its turn present in colloidal suspension or localized onto a surface.

A still further object of the invention is a method for preparing the nanoassembled complexes of general formula (I).

The advantages achievable with the present invention will become more apparent to an expert of the art from the following detailed description of particular embodiments, given for the purposes of non-limiting illustration, and with reference to the following figures.

DETAILED DESCRIPTION OF THE INVENTION

Figure 1:
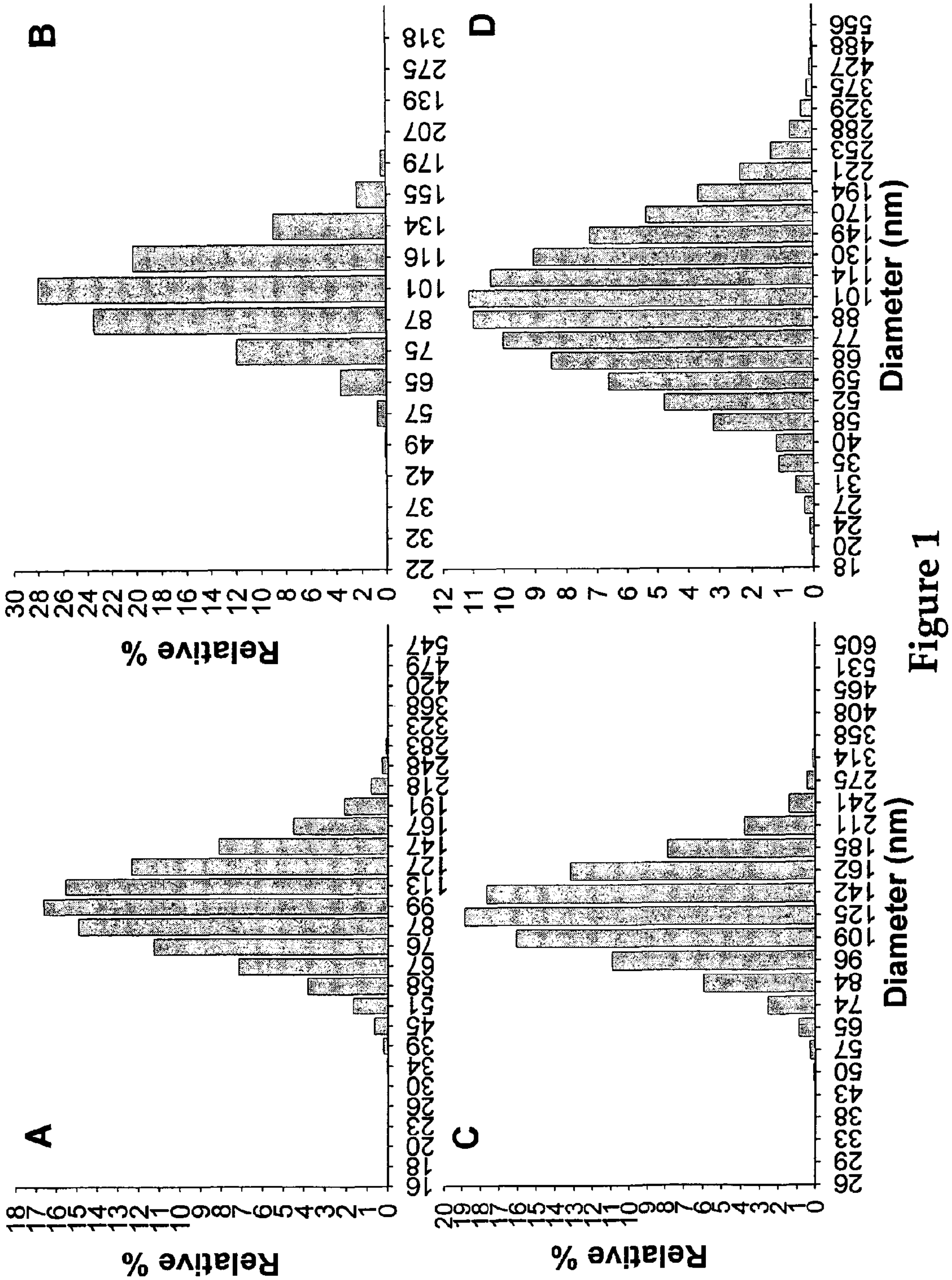
FIG. 1: the figure shows the size distribution (INTENSITY-weighted-GAUSSIAN Analysis) of the particles of the nanoassembled complexes A) Av-pEGFP 3 (sample 1 of examples 1 and 2); B) Av-pEGFP 3-B-$X_a$-$PA_b$-IV-30 (sample 26 of example 2); C) Av-GenNB 2-B (sample 31 of example 4); D) Av-GenNB 2-B-$X_a$-$PA_b$ IV-30 (sample 35 of example 4).

The invention described hereinafter relates to the obtaining and applicative use of nanoassembled complexes in the form of nanoparticles comprising a nucleus of polyavidin, obtained by the nucleation of several avidin units onto one or more nucleic acid molecules, then stabilized by the presence of surface protecting agents so as to be able to remain as discrete and stable entities in saline aqueous solution and free from further non-specific interactions.

With the nanoassembled complexes of the present invention, discrete nanoparticles are obtained which are stabilized against risks of: a) aggregation in aqueous saline environments and b) non-specific interactions with other molecules in solution, by virtue of the presence of protective elements on their surface.

Said protective elements are themselves present on the particle surfaces in controlled and highly defined quantities. Moreover, surface protection according to the preparative method developed by the inventors takes place without destroying the nucleic acid-avidin self-assembled complex and without modifying the total capability of assembled avidins for binding to biotin (i.e. without modifying biotin binding sites).

The size of these nanoparticles can be established from the length of the nucleic acid which is the assembling nucleus of more avidin units, and accordingly, particles characterized by different sizes and different charges on the avidin can be obtained by suitably varying the size of the nucleating nucleic acid (NA).

The characteristics of said particles are precisely defined and their properties can be modulated by the user by varying:

a) the type and size of the nucleating NA;

b) the ratio between avidin and nucleic acid bases;

c) the nature and quantity of the protecting agent present on the surface.

For the purposes of the present invention the compounds object of the same are nanoassembled complexes comprising a nucleus obtained by nucleation secondary to a high affinity interaction of several avidin units onto one or more nucleic acid molecules, and stabilized by a biotinylated surface protecting agent, represented by the general formula (I)

$$NB_nAv_y(B\text{-}X_a\text{-}PA_b)_z \quad (I)$$

wherein:

NB are the single nucleobases of a single or double stranded nucleic acid;

Av is an avidin unit;

B-$X_a$-$PA_b$ is the biotinylated surface protecting agent in which PA is a polymer unit having at least one or two functionalizable residues of which one binds, by a covalent bond either directly or through a spacer X, to a biotin residue B by means of its carboxyl functional group;

n is a number varying from 16 to 10,000,000;

y is an integer equal to or greater than (≧) 1 and being relative to n can vary from (0.0001)·n to (0.0454)·n. If a value comprised in the range (0.0001-0.0454)·n is less than (<)1, then y is equal to (=) 1;

z is an integer equal to or greater than 1 and being relative to y can vary from (0.02)·y to (4)·y. If a value comprised in the range (0.02-4)·y is less than (<) 1, then z is equal to (=) 1;

a is a number varying from 0 to 50 and is preferably comprised from 0 to 10;

b is a number varying from 1 to 128.

If z is less than 4, and hence the biotin binding sites present on the nucleus $NB_nAv_y$ are not saturated by binding with biotin B of the protecting agent (B-$X_a$-$PA_b$), the nanocomplexes of the invention can bind additional biotinylated compounds, different from the protecting agent, onto said binding sites.

Consequently, NB means a nucleic acid consisting of a number of nucleobases (NB) equal to n, with n varying from 16 and 10,000,000, referring to the total number of bases, irrespective of whether the nucleic acid is single or double stranded. Preferably the nucleic acid consists of a base number varying from 30 to 100,000 and more preferably the base number is from 3,000 to 50,000.

Therefore, the term nucleic acid refers equally to:

i) any sequence of a single stranded (ss) or double stranded (ds) deoxyribonucleic acid (DNA) polymer;

ii) any sequence of a ribonucleic acid (RNA) polymer in single stranded form or hybridized with a RNA or a complementary DNA chain;

iii) a sequence, in accordance with the above points, in which a part of or all the bases have been chemically modified.

Moreover, the usable nucleic acid for the nanoassembled complexes of formula (I) can be in linear or circular form, in a relaxed, coiled or supercoiled state.

With reference to the term avidin, avidin is defined as being derived from chicken eggs or another similar source (eggs of birds in general) or from recombinant technology, either in glycosylated or deglycosylated form. Also included are other chemically or genetically modified avidin forms, provided they can assemble onto a single or double stranded nucleic acid as previously established.

In view of the relationship between the number n of NB and the number y of avidin units self-assembling onto the nucleic acid, y is preferably comprised from (0.0001)·n to (0.0357)·n and more preferably comprised from (0.01)·n to (0.0357)·n. For example, if n=10,000, y can vary from 10 to 357, preferably being from 100 to 357. If instead n=100,000, y is comprised from 10 to 3,570 and is preferably from 1,000 to 3,570.

In addition, with reference to the biotinylated surface protecting agent $B\text{-}X_a\text{-}PA_b$:

B means biotin;

PA means preferably a linear unit of a hydrophilic polymer of any molecular weight capable of binding to biotin by a covalent bond, either directly or through a spacer X, by means of the biotin carboxyl group. If PA has two functionizable residues, the second of said residues is free or protected by protecting groups known to an expert of the art, for example a methoxyl group.

If b is greater than 1, and hence PA represents a hydrophilic polymer consisting of several polymer units, these latter are joined together by a further ligand having a number of functionalites equal to or greater than 3 (≧3) of which one binds to the spacer X or to biotin B and the remaining other functional groups bind to the polymer units PA;

X is a spacer consisting of a bifunctional molecule of general formula (II)

$$Y—R—Y' \quad \text{(II)}$$

wherein:

Y, Y' being the same or different from each other are COO—; —NH—; —O—; $SO_2$—; —S—; —SO—; CO—; COS—; —NH—CO—; —NH—CO—; HN—SO—NH—;

R can be an alkyl, an alkenyl, an alkinyl, a cycloalkyl, or an aryl with a carbon atom number comprised from 1 to 20 and preferably from 5 to 20, also optionally substituted.

Therefore, the bond between the spacer X and biotin B and that between the spacer X and the hydrophilic polymer PA can be indiscriminately an amide bond, an amino bond, a carbamide bond, an ester bond, a ketone bond, an ether bond, a thioester bond, a thioether bond, an urea bond, a thiourea, sulphonic or sulphoxide bond.

In view of the relationship between the number y of avidin units and the number z of biotinylated surface protecting agent $B\text{-}X_a\text{-}PA_b$ units, z is comprised from (0.02)·y to (4)·y, and preferably is comprised from (0.4)·y to (4)·y.

For example: in a particle with n=10,000 and y=357 (0.0357·n), z varies from 7 to 1,429, and preferably from 143 to 1,429; in the case of a particle with n=10,000 and y=100, z varies from 2 to 400 and, more preferably, from 40 to 400; in the case of a particle with n=50,000 and y=1,786 (=0.0357n), z varies from 36 to 7,143 and, more preferably, from 714 to 7,143; in the case of a particle with n=50,000 and y=500 (y=0.01n), z varies from 10 to 2,000, and more preferably from 200 to 2,000.

In the nanoassembled complexes of formula (I) of the present invention, the polymer units PA are biocompatible and preferably hydrophilic polymers and are known polymers (Owens D E and Peppas NA 2006 ref. cit.) in which the polymer unit PA has a molecular weight preferably comprised from 400 to 40,000 and more preferably from 1,000 to 20,000. Said polymer units are preferably selected from the group consisting of polyethylene oxide or polyethylene glycol (PEO or PEG) also optionally substituted, a copolymer of polyoxyethylene and polyoxypropylene (PEO-PPO), polyvinylpyrrolidone (PVP), polyacryloylmorpholine (PacM), a polyoxamine, a polylactide (PLA), a polyglycolide (PLG), a copolymer of lactic acid and glycolic acid (PLGA).

More preferably the polymer PA is a substituted polyoxyethylene (PEO) and is therefore characterized by the following formula (III):

$$—(CR^1R^2CR^3R^4O)_m— \quad \text{(III)}$$

where:

$R^1$, $R^2$, $R^3$ and $R^4$ can be independently equal to hydrogen, alkyl, cycloalkyl, aryl, alkenyl, alkinyl, alcoxyl, thioalkoxy, aryloxy and thioaryloxy m is an integer from 2 to 900.

If the polymer consists of several polymer units, and these are bound together by a polyfunctional ligand with functionality equal to or greater than 3 (≧3), said ligand can be lysine, glutamic acid, aspartic acid, cysteine, a dendrimer. The term "dendrimer" means a symmetrical macromolecular compound consisting of branches repeated around a central core consisting of a smaller molecule or a polymeric nucleus. The functional groups present outside the dendrimer, whose number depends on its number of branches, are themselves functionalizable with other molecules including, for example, PA polymers.

Furthermore, if the polymer unit PA is bifunctional, it can further covalently bind, through a second free functional group, to a compound suitable for the uses pursued with the nanoassembled complex, and in particular compounds selected from ligands, sugars, chromophores or fluorophores, drugs, chelating agents for radionuclides, peptides, antibodies, proteins, enzymes and the like.

The preparation of the nanoassembled complexes of the invention comprises three successive steps in aqueous solutions: in the first step nanoparticles consisting of only avidin and nucleic acid are obtained, constituting the central nucleus of the complexes of the invention. The two subsequent steps comprise optionally preparing the biotinylated surface protecting agent $B\text{-}X_a\text{-}PA_b$ but mainly adding said surface protecting agent to the nucleic acid-avidin nanoparticles obtained in the first step.

Therefore, the method for preparing the nanoassembled complexes of general formula $NB_nAv_y(B\text{-}X_a\text{-}PA_b)_z$ (I) comprises at least the steps of:

a) preparing the self-assembled primary nucleus $NB_nAv_y$ by mixing avidin Av with nucleic acid in predefined stoichiometric molar ratios of avidin to nucleobases;

b) mixing the biotinylated surface protecting agent B-X, —$PA_b$ with the previously obtained primary nucleus.

Optionally, preparation of the nanoassemblies of the invention can also comprise preparation of the biotinylated surface protecting agent $B\text{-}X_2\text{-}PA_b$.

The first step is undertaken by mixing, under stirring, the solutions of avidin and nucleic acid, preferably both in salt-free water. In this first step the molar ratios of avidin to nucleobases NB is within the range from 0.44 to 0.0001 and preferably from 0.133 to 0.0044, and more preferably 0.044. The reagents are mixed under continuous stirring at a temperature from 0 to 50° C. for a time between 1 and 600 seconds.

The biotinylated surface protecting agent $B\text{-}X_a\text{-}PA_b$ is prepared by synthesis or, if commercially available, is purchased. Preparation of $B\text{-}X_a\text{-}PA_b$ by synthesis involves conjugating the biotin molecule to the polymer $PA_b$ by chemical means, using classical bioconjugation techniques known to any expert of the art. Subsequently, the previously prepared or purchased biotinylated surface protecting agent $B\text{-}X_a\text{-}PA_b$ is added in a stoichiometrically controlled quantity relative to the concentration of biotin binding sites present in the solution, which are themselves relative to the avidin concentration. The molar ratios of avidin: B-$X_a$-$PA_b$ are hence comprised between 4 and 0.02.

Addition of the biotinylated surface protecting agent B-$X_a$-$PA_b$ is also carried out under stirring in aqueous solutions at a controlled temperature from 0 to 50° C. for a time between 1 and 120 minutes.

Moreover, the nanoassembled complexes of the invention can be prepared by a method in which steps a) and b) are substantially inverted, hence the preparation method can comprise:

a) adding the biotinylated surface protecting agent B-$X_a$-$PA_b$ to the avidin in pre-defined stoichiometric molar ratios of biotin to avidin;

b) adding nucleic acid to the conjugate $Av_y$(B-$X_a$-$PA_b$)$_z$ obtained in the preceding step in pre-defined stoichiometric molar ratios of avidin to nucleobases.

The preparation conditions are the same as those previously described for the first method.

If necessary, as well as the aforementioned steps, whether the nanoassembled complexes are prepared by the first or second process, the preparation method can further comprise the purification of the particles from any monomeric avidin eventually present in the solution as a residue of the first step. Purification can be undertaken after either step a) or step b).

Purification of the nanoassembled complexes from any monomeric avidin present in solution can be carried out by known methods, for example ultrafiltration or size exclusion chromatography. In the case of ultrafiltration, suitable systems are used, characterized by a cut-off equal to or greater than (≧) 100 kDa. In the case of size exclusion chromatography, chromatographic media are used which are suitable for retaining protein molecules of sizes up to (<) 200 kDa.

If the biotin binding sites present on the avidin of the nucleus are not saturated by the biotinylated surface protecting agent B-$X_a$-$PA_b$ the preparation method can also comprise a further optional step of adding additional biotinylated compounds equal or different each other.

With the previously described preparation methods, nanoassembled complexes having the features of nanoparticles of any size can be obtained. In particular, said nanoassembled complexes are in form of nanoparticles of at least 10 nm in size and preferably from 50 to 1,000 nm in size.

The use of nanoassembled complexes in nanoparticulate form herein described extends to all currently known applications of the avidin-biotin system, for which they act as "amplification" systems. Examples of these applications include their use as: a) detection means in in vitro diagnostics; b) amplifiers in the localization and patterning of molecules on surfaces (for example microarrays, protein chips and DNA); c) instruments for in vivo diagnostics; d) systems for active or passive is targeting of drugs.

The use will depend on the nature of the biotinylated compounds which can further be introduced onto nanoassembly surfaces through biotin binding sites present on the avidin and not saturated by binding with biotin of the protecting agent B-$X_a$-$PA_b$.

EXPERIMENTAL PART

Some examples of the preparation of the nanoassembly compounds of the invention and their characterization wilt be given hereinafter by way of non-limiting illustration.

In particular, the nanoassembly compounds obtained by the previously described preparation were characterized by:

a) their size, using light scattering and electronic microscopy techniques;

b) the degree of dispersion, using light scattering;

c) the number of biotin binding sites available for introducing additional biotinylated functions. This assessment was carried out using the HABA assay, as described in the literature (Green N M *Biochem. J.* 1965, 94: 23C-24C);

d) the speed of aggregation in a buffered medium, using light scattering techniques;

e) their stability to freezing and thawing, and to lyophilization, using light scattering techniques.

Example 1

Preparation and Characterization of Nanoassemblies Obtained with Plasmid DNA and Avidin in Different Molar Ratios without Addition of a Surface Protector The complexes were prepared by mixing aqueous solutions of avidin (Av, Belovo, Belgium) and nucleic acid (pNM, plasmid p-EGFP Cl (Clonetech#6084-1) (4.7 Kb)) in varying molar ratios as given in table 1 below.

The solutions were left to equilibrate for an hour at 0° C. in an ice bath, and after centrifugation (15,000 rpm for 5 minutes), the sizes of the nanoassemblies in solution were analyzed by light scattering using an instrument system consisting of a Spectra Physics Stabilite 2017 laser, a Pacific Scientific "Nicomp 370 Computing Autocorrelator" and a system for temperature controlling the samples.

TABLE 1

Molar ratio of avidin:plasmid poly-nucleic acid and dimensional characteristics of the particles in deionized water

| Sample | Avidin:Nucleobase (NB) in preparation solution (y:n) | Avidin:plasmid (pNB) in solution | Mean diameter of nanoassemblies in solution (nm) |
|---|---|---|---|
| 1- Av-pEGFP 3.0 | 0.125:1 | 1175:1 | 106 ± 33 |
| 2- Av-pEGFP 2.0 | 0.0833:1 | 783:1 | 124 ± 51 |
| 3- Av-pEGFP 1.5 | 0.0625:1 | 587:1 | 144 ± 55 |
| 4- Av-pEGFP 0.5 | 0.0208:1 | 196:1 | 148 ± 68 |

The size distribution measured on the first sample is given in FIG. 1. From the figure said assembly can be seen to be characterized by a moderate polydispersivity. The data in table 1 also show that the sizes and polydispersivity of the nanoassembly increase as the yin ratio decreases, indicating that as this value decreases, the degree of condensation of the nucleic acid molecule in the assembly is less. The size variation as y/n varies is however limited to within the values of about 70 to 200 nm.

Example 2

Preparation and Characterization of Nanoassemblies Obtained with Plasmid DNA, Avidin and Surface Protecting Agents Different quantities of the various surface protecting agents (B-$X_a$-$PA_b$) were added to sample 1 Av-pEGFP 3, prepared as described in example 1, using B-$X_a$-$PA_b$: avidin molar ratios varying between 0 and 2.4 as shown in table 2. Five different B-$X_a$-$PA_b$ agents were used (I, IIa, lib, III and IV), whose chemical formulas are given as follows:

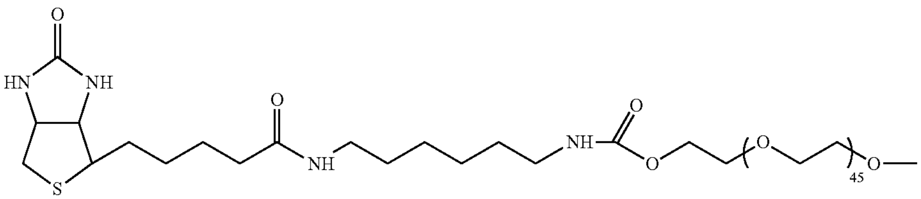
Biotin-CO—NH-(CH2)6-NH—O—CO-mPEG2000(B-PA I)
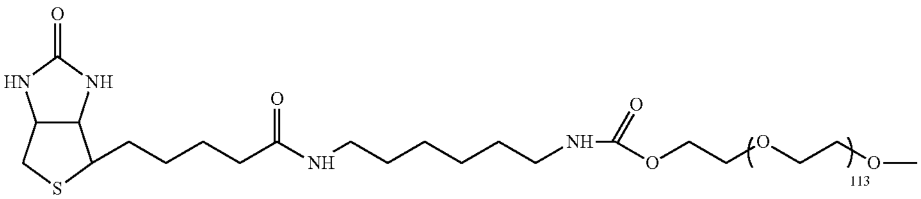
Biotin-CO—NH—$(CH_2)_6$—O—CO—NH-mPEG5000 (B-PA IIa)
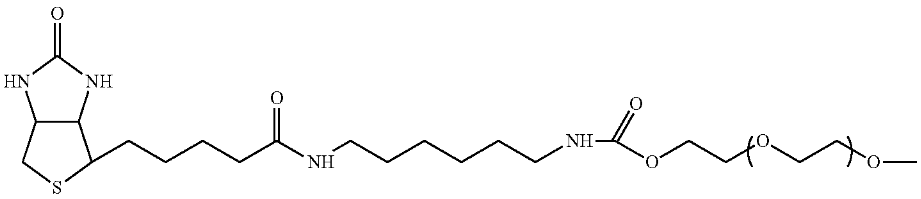
Biotin-CO—NH-(CH2)6-NH—O—CO-mPEG5000(B-PA IIb)
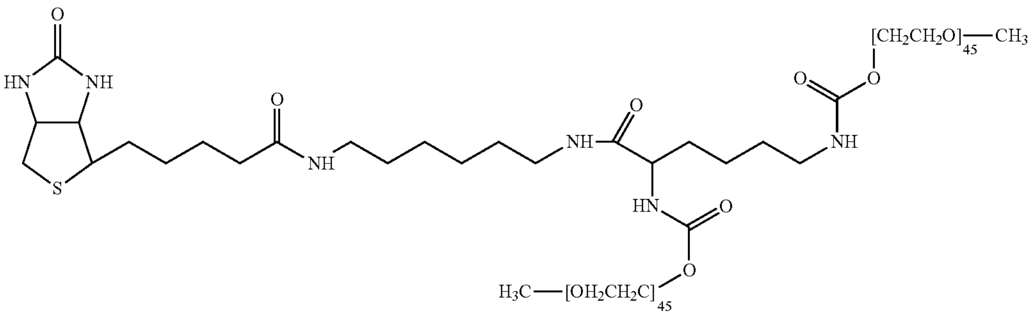
Biotin-CO—NH—$(CH_2)_6$—NH-Lys-$(mPEG2000)_2$(B-PA III)
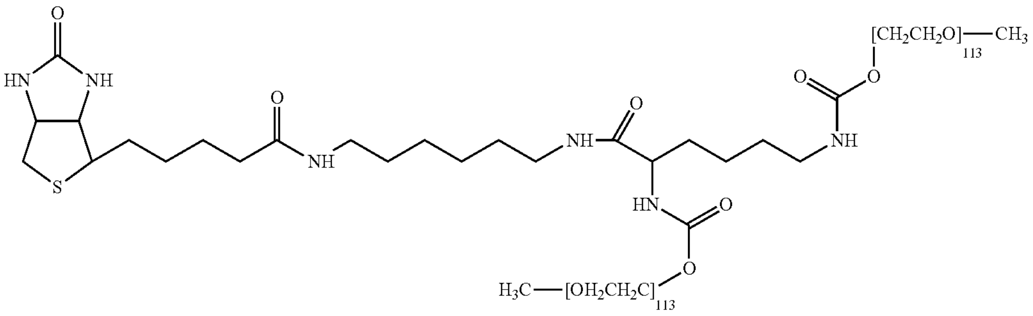
Biotin-CO—NH-(CH2)6-NH-Lys-$(mPEG5000)_2$(B-PA IV)

Said protecting agents B-$X_a$-$PA_b$ were synthesized and characterized as described below.

B-$X_a$-$PA_b$ I: was obtained by condensing the 6-amino-n-hexylamide of biotin with the N-hydroxysuccinimidyl carbonate of monomethoxy polyethylene glycol 2,000 (Monfardini C, Schiavon O et al. *Bioconjugate Chemistry* 1995, 6: 62-69).

B-$X_a$-$PA_b$ IIa: was obtained by condensing α-amino, ω-methoxy-polyethylene glycol 5,000 (Fluka cat#06679) with the N-hydroxysuccinimidyl carbonate of biotinyl-n-hexanolamide (Morpurgo M, Bayer E A et al. *J. Biochem. Biophys. Meth.* 1999, 38: 17-28).

B-$X_a$-$PA_b$ IIb: was obtained in a similar manner to B-$X_a$-$PA_b$ I using monomethoxy polyethylene glycol 5,000 instead of 2,000.

B-$X_a$-$PA_b$ III: was obtained by condensing the N-hydroxysuccinimidyl carbonate of monomethoxy polyethylene glycol 2,000 with the amino groups of the amide of 2,6 diaminohexanoic acid and with biotinyl-n-hexyldiamine (2,6-diamino-hexanoic acid (6-biotinylamidohexyl)-amide).

B-$X_a$-$PA_b$ IV: was obtained in a similar manner to B-$X_a$-$PA_b$ III using monomethoxy polyethylene glycol 5,000 instead of 2,000.

The dimensions of the final nanoassembled complexes in the assembling solutions were measured by light scattering, as described in example 1. The size results are summarized in table 2 and FIG. 1.

TABLE 2

Composition of the assembling solutions and dimensional characteristics of the relative nanoassemblies described in example 2.

| Sample | Type of B-$X_a$-$PA_b$ | % occupied BBS | B-$X_a$-$PA_b$: avidin (z/y) | Mean diameter (nm) |
|---|---|---|---|---|
| 1- Av-pEGFP 3 (ex. 1) | None | 0 | 0 | 106 ± 33 |
| 5- Av-pEGFP3 - B-$X_a$-$PA_b$ I-20 | Biotin-mPEG2000 (I) | 20 | 0.8 | 88 ± 20 |
| 6- Av-pEGFP3 - B-$X_a$-$PA_b$ I-30 | Biotin-mPEG2000 (I) | 30 | 1.2 | 96 ± 33 |
| 7- Av-pEGFP3 - B-$X_a$-$PA_b$ I-40 | Biotin-mPEG2000 (I) | 40 | 1.6 | 85 ± 25 |
| 8- Av-pEGFP3 - B-$X_a$-$PA_b$ I-50 | Biotin-mPEG2000 (I) | 50 | 2.0 | 88 ± 26 |
| 9- Av-pEGFP3 - B-$X_a$-$PA_b$ I-60 | Biotin-mPEG2000 (I) | 60 | 2.4 | 92 ± 23 |
| 10- Av-pEGFP3 - B-$X_a$-$PA_b$ IIa-20 | Biotin-mPEG5000 (IIa) | 20 | 0.8 | 91 ± 31 |
| 11- Av-pEGFP3 - B-$X_a$-$PA_b$ IIa-30 | Biotin-mPEG5000 (IIa) | 30 | 1.2 | 87 ± 21 |
| 12- Av-pEGFP3 - B-$X_a$-$PA_b$ IIa-40 | Biotin-mPEG5000 (IIa) | 40 | 1.6 | 90 ± 26 |
| 13- Av-pEGFP3 - B-$X_a$-$PA_b$ IIa-50 | Biotin-mPEG5000 (IIa) | 50 | 2.0 | 88 ± 32 |
| 14- Av-pEGFP3 - B-$X_a$-$PA_b$ IIa-60 | Biotin-mPEG5000 (IIa) | 60 | 2.4 | 96 ± 34 |
| 15- Av-pEGFP3 - B-$X_a$-$PA_b$ IIb-20 | Biotin-mPEG5000 (IIb) | 20 | 0.8 | 111 ± 28 |
| 16- Av-pEGFP3 - B-$X_a$-$PA_b$ IIb-30 | Biotin-mPEG5000 (IIb) | 30 | 1.2 | 109 ± 39 |

TABLE 2-continued

Composition of the assembling solutions and dimensional characteristics of the relative nanoassemblies described in example 2.

| Sample | Type of B-$X_a$-$PA_b$ | % occupied BBS | B-$X_a$-$PA_b$: avidin (z/y) | Mean diameter (nm) |
|---|---|---|---|---|
| 17- Av-pEGFP3 - B-$X_a$-$PA_b$ IIb-40 | Biotin-mPEG5000 (IIb) | 40 | 1.6 | 112 ± 14 |
| 18- Av-pEGFP3 - B-$X_a$-$PA_b$ IIb-50 | Biotin-mPEG5000 (IIb) | 50 | 2.0 | 115 ± 28 |
| 19- Av-pEGFP3 - B-$X_a$-$PA_b$ IIb-60 | Biotin-mPEG5000 (IIb) | 60 | 2.4 | 116 ± 36 |
| 20- Av-pEGFP3 - B-$X_a$-$PA_b$ III-20 | Biotin-Lys-$(mPEG2000)_2$ (III) | 20 | 0.8 | 91 ± 28 |
| 21- Av-pEGFP3 - B-$X_a$-$PA_b$ III-30 | Biotin-Lys-$(mPEG2000)_2$ (III) | 30 | 1.2 | 91 ± 22 |
| 22- Av-pEGFP3 - B-$X_a$-$PA_b$ III-40 | Biotin-Lys-$(mPEG2000)_2$ (III) | 40 | 1.6 | 90 ± 27 |
| 23- Av-pEGFP3 - B-$X_a$-$PA_b$ III-50 | Biotin-Lys-$(mPEG2000)_2$ (III) | 50 | 2.0 | 93 ± 32 |
| 24- Av-pEGFP3 - B-$X_a$-$PA_b$ III-60 | Biotin-Lys-$(mPEG2000)_2$ (III) | 60 | 2.4 | 96 ± 31 |
| 25- Av-pEGFP3 - B-$X_a$-$PA_b$ IV-20 | Biotin-Lys-$(mPEG5000)_2$ (IV) | 20 | 0.8 | 101 ± 41 |
| 26- Av-pEGFP3 - B-$X_a$-$PA_b$ IV-30 | Biotin-Lys-$(mPEG5000)_2$ (IV) | 30 | 1.2 | 101 ± 20 |
| 27- Av-pEGFP3 - B-$X_a$-$PA_b$ IV-40 | Biotin-Lys-$(mPEG5000)_2$ (IV) | 40 | 1.6 | 100 ± 24 |
| 28- Av-pEGFP3 - B-$X_a$-$PA_b$ IV-50 | Biotin-Lys-$(mPEG5000)_2$ (IV) | 50 | 2.0 | 101 ± 20 |
| 29- Av-pEGFP3 - B-$X_a$-$PA_b$ IV-60 | Biotin-Lys-$(mPEG5000)_2$ (IV) | 60 | 2.4 | 100 ± 34 |

Figure 2:
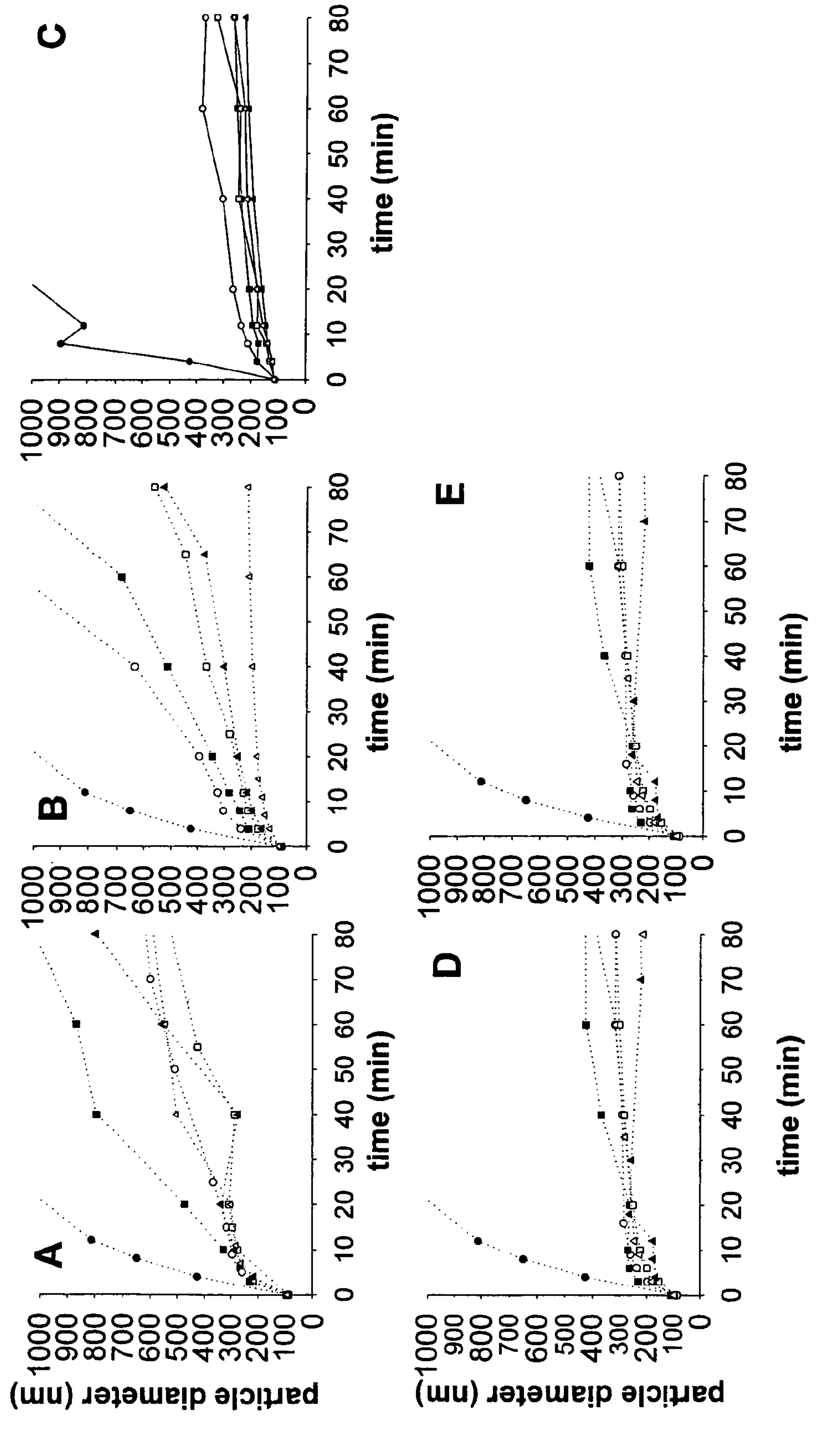
FIG. 2: the figure shows the kinetics of aggregation in a buffered solution of the different nanoassembled complexes of example 2 as a function of the type of B-$X_a$-$PA_b$ used and its quantity. The composition of the various formulations are summarized in table 2. A: B-$X_a$-$PA_b$ I, % total occupied biotin binding sites (BBS=Biotin Binding Sites) equal to 0 (●), 20 (O), 30 (■), 40 (□), 50 (▲), 60 (Δ) %; B: B-$X_a$-$PA_b$ IIa, % of occupied BBS equal to 0 (●), 20 (O), 30 (■), 40 (□), 50 (▲), 60 (Δ) %; C: B-$X_a$-$PA_b$ IIb, % of occupied BBS equal to 0 (●), 20 (O), 30 (■), 40 (□), 50 (□), 60 (▲) %; D: B-$X_a$-$PA_b$ III, % of occupied BBS equal to 0 (●), 20 (O), 30 (■), 40 (□), 50 (▲), 60 (Δ) %; E: B-$X_a$-$PA_b$ IV, % of occupied BBS equal to 0 (●), 20 (O), 30 (■), 40 (□), 50 (▲), 60 (Δ) %.

All the samples, initially prepared in salt- and ion-free water, were then diluted in PBS buffer and their aggregation rate was measured by light scattering. The aggregation kinetics are shown in FIG. 2. It can be seen from the figure that when the B-$X_a$-$PA_b$s are introduced onto the surfaces of the nanoassemblies they slow aggregation of the latter, in a salt-containing environment, until they inhibit it completely. The protective efficacy of each B-$X_a$-$PA_b$ increases with increasing surface concentration of B-$X_a$-$PA_b$. The protective efficacy also depends on the type of B-$X_a$-$PA_b$, with B-$X_a$-$PA_b$ IV and B-$X_2$-$PA_b$ IIb being the most effective of all those tested.

Example 3

Preparation and Characterization of Nanoassemblies Obtained with Plasmid DNA and Avidin, and Purification by Ultrafiltration Alexa-Fluor546-biocytin (Molecular probes # A12923) was added to sample 1 Av-pEGFP 3, prepared as described in example 1, in a quantity equal to that needed to saturate 2% of total biotin binding sites. The prepared product was subjected to various ultrafiltration steps using Vivaspin 100K PES membranes (Sartorius, 100,000 Da cut-off) so as to enable monomeric but not nanoassembled avidin to pass through. The avidin concentration in the supernatant and in the filtrate was determined by fluorescence, based on the signal of the Alexa-Fluor546 fluorophore. The supernatant obtained after four ultrafiltration steps was analyzed by light scattering. The avidin:NB ratio in the nanoparticulate system was calculated from the avidin concentration present therein with the assumption that the DNA present was the same as that present prior to ultrafiltration.

TABLE 3

Composition of the solution containing nanoparticles before and after their purification expressed as avidin:nucleobase ratio (y/n)

| Sample | Avidin:Nucleobase (NB) (y/n) | Size (nm) |
|---|---|---|
| 1- Av-pEGFP 3 (ex. 1) before purification | 0.125:1 | 106 ± 33 |
| 1- Av-pEGFP 3 (ex. 1) after purification | 0.0375:1 | 152 ± 68 |

From the results given in the table it is apparent that ultrafiltration treatment is able to remove excess monomeric avidin introduced in the preparative stage. Particle sizes are found to be slightly larger than those recorded before purification. This difference (not statistically relevant) is probably ascribable to the lower level of DNA packing recorded as the y/n ratio in solution decreases, as already described in example 1.

Example 4

Preparation and Characterization of Nanoassemblies Obtained with Genomic DNA and Avidin in Different Molar Ratios, with and without Addition of Surface Protector The nanocomplexes were prepared by mixing aqueous solutions of avidin (Av, Belovo, Belgium) and fragmented bacterial genomic nucleic acid (Gen pNB, Sigma cat #D1760) (average size about 16-24 Kb) in a variable molar ratio (see table 4). The solutions were left for an hour at 0° C.

in an ice bath and after centrifugation (15,000 rpm for 5 minutes) the dimensions of the nanoassemblies in solution (table 4) were analyzed by light scattering as described in example 1.

TABLE 4

Molar ratio of avidin:genomic nucleic acid: B-$X_a$-$PA_b$, and dimensional characteristics of the particles in deionized water

| Sample | Avidin:Nucleobase (NB) in solution | Avidin: nucleic acid (Gen pNB) in solution | B-$X_a$-$PA_b$:Av | Mean diameter of nanoassemblies in solution (nm) |
|---|---|---|---|---|
| 30- Av-GenpNB 3 | 0.125:1 | 5000:1 | 0 | 132 ± 75 |
| 31- Av-GenpNB 2 | 0.0833:1 | 3333:1 | 0 | 133 ± 37 |
| 32- Av-GenpNB 1.5 | 0.0625:1 | 2500:1 | 0 | 160 ± 23 |
| 33- Av-GenpNB 0.75 | 0.0312:1 | 1666:1 | 0 | 140 ± 18 |
| 34- Av-GenpNB 3-B-$X_a$-$PA_b$ IV 30 | 0.125:1 | 5000:1 | 1.2 | nd |
| 35- Av-GenpNB 2-B-$X_a$-$PA_b$ IV 30 | 0.0833:1 | 3333:1 | 1.2 | 107 ± 50 |
| 36- Av-GenpNB 1.5 B-$X_a$-$PA_b$ IV 30 | 0.0625:1 | 2500:1 | 1.2 | 112 ± 62 |
| 37- Av-GenpNB 0.75-B-$X_a$-$PA_b$ IV 30 | 0.0312:1 | 1666:1 | 1.2 | 205 ± 79 |

Example 5

First Comparison of Efficiency of Avidin in Monomeric Form and in Nanocomplexed Form with Nucleic Acid, in Dot Blot Fluorescent Detection A biotinylated antibody (anti-hPSMA) was immobilized by spotting (1 μl) onto nitrocellulose membranes. The membranes were blocked by immersing into PBS containing 2% w/v of BSA (PBS/BSA) then treated with solutions containing avidin (1.3 μg/ml in PBS/BSA), with previously added biotin-Alexa-Fluor® in a quantity so as to saturate 25% of total biotin binding sites. The avidin in said solutions was used in the monomeric or nanoassembled form (table 5).

TABLE 5

Compositional characteristics of the detecting avidin solutions used in the dot blot fluorescent assay

| Sample | Form of avidin | Avidin:Nucleobase (NB) (y/n) | B-$X_a$-$PA_b$: Avidin (z/y) |
|---|---|---|---|
| 38- Av. | Monomeric | — | 1 |
| 39- Av-pEGFP 1.5 B-$X_a$-$PA_b$ IV 25 | Nano-particulate | 0.0625 | 1 |
| 40- Av-pEGFP 0.75 B-$X_a$-$PA_b$ IV 25 | Nano-particulate | 0.0312 | 1 |

Figure 3:
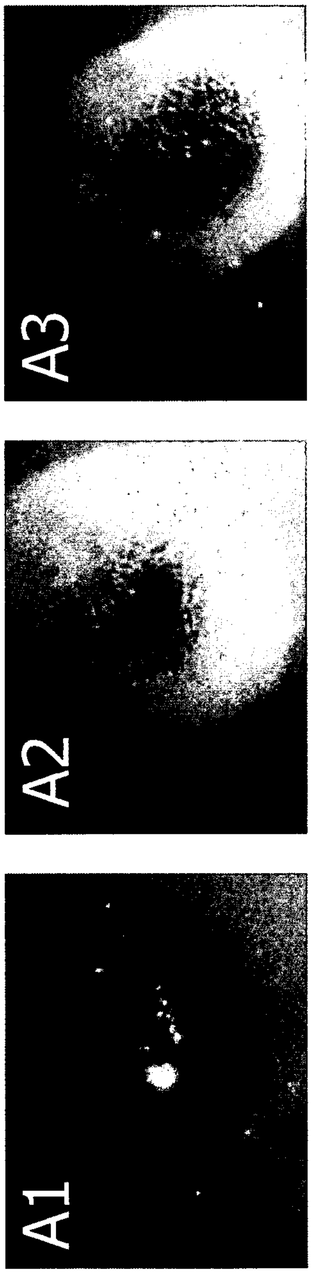
FIG. 3: the figure shows fluorescent microscope images of membranes used in an assay, with dot blot fluorescent detection, comparing avidin in monomeric form and in nanocomplexed form with nucleic acid. Incubation was carried out using avidin-biotin-Alexa solutions at 1.3 μg/ml. A1: monomeric avidin (sample 38 example 5); A2: Av-pEGFP 1.5 B-$X_2$-$PA_b$ IV-25 (sample 39 example 5); A3: Av-pEGFP 0.75 B-$X_a$-$PA_b$ IV-25 (sample 40 example 5).

After 2 hours of incubation at ambient temperature, the membranes were washed with PBS and visualized with a fluorescence microscope (FIG. 3). It can be seen from the figure that nanoassembled avidin is more effective at detecting the immobilized sample on the membrane.

Example 6

Second Comparison of Efficiency of Avidin in Monomeric Form and in Nanocomplexed Form with Nucleic Acid, in Dot Blot Fluorescent Detection Varying quantities of biotinylated BSA (100, 50, 20, 10, 5, 2 ng of protein corresponding respectively to 10, 5, 2, 1, 0.5 and 0.2 pmoles of biotin/spot) were immobilized by spotting (0.1 μl) onto nitrocellulose membranes. The membranes were blocked by immersing into PBS containing 2% w/v of BSA (PBS/BSA) then treated with solutions containing avidin (5 μg/ml in PBS/BSA), with previously added biotin-Alexa-Fluor® in a quantity so as to saturate 40% of total biotin binding sites. The avidin in said solutions was used in the monomeric or nanoassembly form (table 6).

TABLE 6

Compositional characteristics of the detecting solutions used in the 2nd dot blot fluorescent assay

| Sample | Form of avidin | Avidin:Nucleobase (NB) (y/n) | $B-X_a-PA_b$: Avidin (z/y) |
|---|---|---|---|
| 38- Av. | Monomeric | — | 1 |
| 41- Av-pEGFP 0.5 $B-X_a-PA_b$ IV 25 | Nano-particulate | 0.0208 | 1 |

Figure 4:
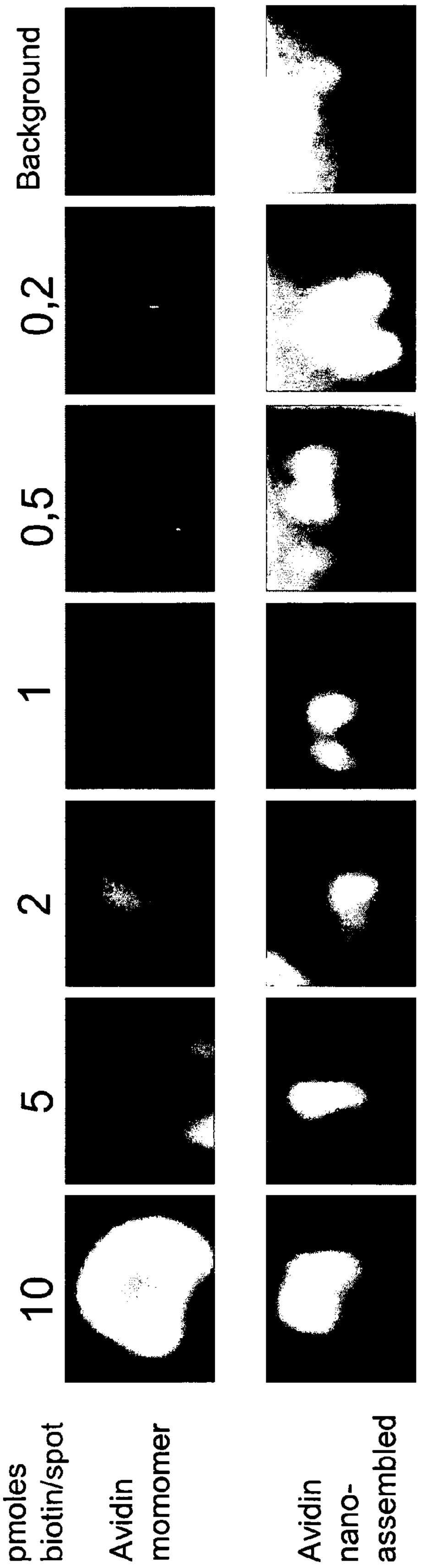
FIG. 4: the figure shows fluorescent microscope images of membranes used in a further assay, with dot blot fluorescent detection, comparing avidin in monomeric from and in nanocomplexed form with nucleic acid. Incubation was carried out using avidin-biotin-Alexa solutions at 5 μg/ml in monomeric form (sample 38 of examples 5 and 6) and in nanoassembly form (sample 41 example 6).

After 2 hours of incubation at ambient temperature, the membranes were washed with PBS then visualized with a fluorescence microscope (FIG. 4). It can be seen from the figure that the detection limit using monomeric avidin is equal to 1 pmole of biotin, whereas when avidin is used in the nanoparticulate form, biotin is visible even in quantities equal to or less than 0.2 pmoles. The detection limit with the nanoassembly system was not achieved in this experiment.

Example 7

Stability to Freezing/Thawing of the Nanoassemblies in the Absence and Presence of $B-X_a-PA_b$ Agents The nanoassembly samples obtained with genomic DNA as given in example 4 were subjected to a freeze-thaw cycle. The size measurements of the particles present in solution after thawing were compared to those of the same preparations before treatment. The results are shown in table 7.

TABLE 7

Dimensional characteristics of the nanoassemblies before and after freezing/thawing

| Sample | Mean diameter of nanoassemblies in solution (nm) before freezing | Mean diameter of nanoassemblies in solution (nm) after freezing and thawing |
|---|---|---|
| 30- Av-GenpNB 3 | 132 ± 75 | >1000 |
| 31- Av-GenpNB 2 | 133 ± 37 | >1000 |
| 32- Av-GenpNB 1.5 | 160 ± 23 | >1000 |
| 33- Av-GenpNB 0.75 | 140 ± 18 | >1000 |
| 34- Av-GenpNB 3- $B-X_a-PA_b$ IV 30 | Nd | 143 ± 75 |
| 35- Av-GenpNB 2- $B-X_a-PA_b$ IV 30 | 107 ± 50 | 210 ± 147 |
| 36- Av-GenpNB 1.5 $B-X_a-PA_b$ IV 30 | 112 ± 62 | 193 ± 155 |
| 37- Av-GenpNB 0.75- $B-X_a-PA_b$ IV 30 | 205 ± 79 | 129 ± 55 |

It can be deduced from the results that the particles devoid of protection agent are not resistant to the freeze-thaw process, subsequent to which they aggregate irreversibly. When instead the protecting agent $B-X_a-PA_h$ is present on the surface, aggregation is inhibited.

Example 8

Figure 5:
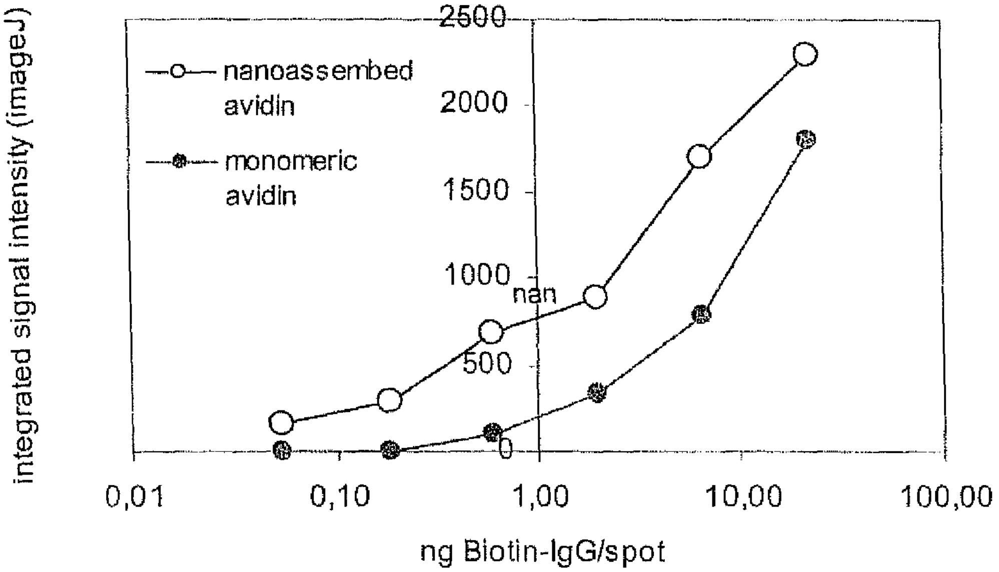
FIG. 5: the figure shows the comparison of detecting efficiency of avidin in a monomeric (○) ad nanocomplexed (●) form with nucleic acid, in a dot blot with enzyme (HRP)-linked detection system. Spot detection was achieved upon incubation with biotin-HRP and development with DAB substrate of membranes previously incubated with avidin solutions at 5 μg/ml in monomeric form (sample 38 of examples 5 and 6 and 7) and in nanoassembly form (sample 42 example 7).

Comparison of Efficiency of Avidin in Monomeric Form and in Nanocomplexed Form with Nucleic Acid, in an Enzyme-Linked Detection System Varying quantities of biotinylated-IgG (IgG-B) (0.054, 0.18, 0.6, 2.0, 6.7 and 22.3 ng of protein were immobilized by spotting (0.5 μl) onto nitrocellulose membranes. The membranes were blocked by immersing into PBS containing 2% w/v of BSA (PBS/BSA) then treated with solutions containing avidin (5 μg/ml in PBS/BSA). The avidin in said solutions was used in the monomeric or nanoassembly form (table 7). After 1 hour of incubation at ambient temperature, the membranes were washed with PBS and incubated (1 h) with biotin-horseradish peroxidase (Sigma-Aldrich, 4 μg/ml in PBS/BSA). Membrane development was carried out with diaminobenzidine (DAB). Spot density was analyzed through the ImageJ software and translated into the graph of FIG. 5. It can be seen from the figure that the detection limit using monomeric avidin is equal to 0.6 ng of IgG-B, whereas when avidin is used in the nanoparticulate form, IgG is visible even in quantities equal to or less than 0.054 ng. The detection limit with the nanoassembly system was not achieved in this experiment.

TABLE 7

Compositional characteristics of the detecting avidin solutions used in the enzyme-linked dot blot assay

| Sample | Form of avidin | Avidin:Nucleobase (NB) (y/n) | $B-X_a-PA_b$: Avidin (z/y) |
|---|---|---|---|
| 38- Av. | Monomeric | — | 1 |
| 42- Av-pEGFP 0.95 $B-X_a-PA_b$ IV 25 | Nano-particulate | 0.0396 | 1 |

The invention claimed is:

1. Nanoassembled complexes comprising a nucleus obtained by means of high affinity interaction between one or more avidin units and one or more nucleic acid molecules, wherein said nucleus is stabilized by a biotinylated surface protecting agent, represented by the general formula (I)

$$NB_nAv_y(B-X_a-PA_b)_z \qquad (I)$$

wherein:

NB are the single nucleobases of a single or double stranded nucleic acid;

Av is an avidin unit;

$B-X_a-PA_b$ is the biotinylated surface protecting agent in which PA is a polymer having at least one or two functionalizable residues of which one binds, by a covalent bond either directly or through a spacer X, to a biotin residue B by means of carboxyl functional group of said residue B selected from the group consisting of polyethylene oxide or polyethylene glycol (PEO or PEG) optionally substituted, a polyoxyethylene and polyoxypropylene copolymer (PEO-PPO);

n is a number greater than 16;

y is an integer equal to or greater than 1 (≧1) and is related to n as having a value in the range from (0.0001)·n to (0.0454)·n with the proviso that if a value in the range (0.0001-0.0454)·n is less than 1 (<1), then y is equal to 1 (=1);

z is an integer equal to or greater than 1 (≧1) and is related to y as having a value in the range from (0.02)·y to (4)·y with the proviso that if a value in the range (0.02-4)·y is less than 1 (<1), then z is equal to 1 (=1);

a is a number from 0 to 50;

b is a number from 1 to 128.

2. Nanoassembled complexes according to claim 1, wherein y is in the range from (0.0001)·n to (0.0357)·n.

3. Nanoassembled complexes according to claim 2, wherein y is in the range from (0.01)·n to (0.0357)·n.

4. Nanoassembled complexes according to claim 1, wherein z is in the range from (0.4)·y to (4)·y.

5. Nanoassembled complexes according to claim 1, wherein a is in the range from 0 to 10.

6. Nanoassembled complexes according to claim 1, wherein the single or double stranded nucleic acid is selected from the group consisting of any sequence of a single or double stranded deoxyribonucleic acid (DNA) polymer, any sequence of a ribonucleic acid (RNA) polymer in single stranded form or hybridized with a RNA or a complementary DNA chain and a sequence thereof in which a part of or all the bases have been chemically modified.

7. Nanoassembled complexes according to claim 1, wherein the polymer PA has a molecular weight in the range from 400 to 40,000.

8. Nanoassembled complexes according to claim 7, wherein the polymer PA has a molecular weight in the range from 1,000 to 20,000.

9. Nanoassembled complexes according to claim 1, wherein the polymer PA is a substituted polyoxyethylene (PEO) represented by the formula (III)

$$—(CR^1R^2CR^3R^4O)_m—$$

wherein:

$R^1$, $R^2$, $R^3$ and $R^4$ can be independently equal to hydrogen, alkyl, cycloalkyl, aryl, alkenyl, alkinyl, alcoxyl, thioalkoxy, aryloxy and thioaryloxy, m is an integer from 2 to 900.

10. Nanoassembled complexes according to claim 1, wherein if b is other than 1 the polymers PA are bound together by a further polyfunctional ligand having at least 3 functional groups, of which one binds to biotin B directly or indirectly through a spacer X and the remaining functional groups bind to the polymers PA.

11. Nanoassembled complexes according to claim 10, wherein the polyfunctional ligand is selected from the group consisting of lysine, glutamic acid, aspartic acid, cysteine and a dendrimer.

12. Nanoassembled complexes according to claim 1, wherein if the polymer PA has two functionalizable residues, the second of said residues is free or protected by a protecting group.

13. Nanoassembled complexes according to claim 1, wherein if the polymer PA has two functionalizable residues, the second of said residues further covalently binds, through said second functional group, to a compound selected from ligands, sugars, chromophores or fluorophores, drugs, chelating agents for radionuclides, antibodies, peptides, proteins and enzymes.

14. Nanoassembled complexes according to claim 1, wherein the spacer X is a bifunctional compound represented by the general formula (II)

$$Y—R—Y' \quad (II)$$

wherein:

Y, Y' being the same or different from each other are —COO—; —NH —; —O—; $SO_2$—; —S—; —SO—; —CO—; —COS—; —NH—CO—; —NH—COO—; HN—SO—NH—;

R can be an alkyl, an alkenyl, an alkinyl, a cycloalkyl, or an aryl, with a carbon atom number of from 1 to 20 optionally substituted.

15. Nanoassembled complexes according to claim 14, wherein R is selected from the group consisting of an alkyl, an alkenyl, an alkinyl, a cycloalkyl, or an aryl, with a carbon atom number of from 5 to 20 optionally substituted.

16. Nanoassembled complexes according to claim 1, wherein, if z is less than 4, further comprises biotinylated compounds being the same as or different from each other, and different from the protecting agent B-$X_a$-$PA_b$.

17. Nanoparticles comprising nanoassembled complexes according to claim 1.

18. Nanoparticles according to claim 17 having a mean diameter dimension of at least 10 nm.

19. Nanoparticles according to claim 18, wherein the mean diameter dimensions are comprised from 50 to 1,000 nm.

20. Nanoassembled complexes according to claim 1 obtained by:

a) preparing the self-assembled primary nucleus $NB_nAv_y$ by mixing avidin Av with the nucleic acid in stoichiometrically predefined molar ratios of nucleobases NB to avidin Av; and b) mixing the biotinylated surface protecting agent B-$X_a$-$PA_b$ with the primary nucleus $NB_nAv_y$ obtained in step a), the latter being added in stoichiometrically predefined molar ratios of avidin Av to the biotin B of B-$X_a$-$PA_b$; or a) preparing the conjugated compound $Av_y$(B-$X_a$-$PA_b$)$_z$ by mixing avidin Av with the surface protecting agent B-$X_a$-$PA_b$ in stoichiometrically predefined molar ratios of the biotin B of B-$X_a$-$PA_b$ to avidin Av; and b) mixing the conjugated compound $Av_y$(B-$X_a$-$PA_b$)$_z$ obtained in step a) with nucleic acid added in stoichiometrically predefined molar ratios of avidin Av to nucleobases NB;

wherein the mixing of nucleobases with avidin or $Av_y$(B-$X_a$-$PA_b$)$_z$ is carried out in salt-free aqueous solutions at a temperature from 0° C. to 50° C. and the stoichiometrically predefined molar ratios of nucleobases NB to avidin are in the range from 0.44 to 0.0001.

21. Nanoassembled complexes according to claim 20, comprising the additional step of purifying the compound obtained in step a) or the nanoassembled complex obtained in step b) from monomeric avidin.

22. Nanoassembled complexes according to claim 20, comprising the additional step of further adding biotinylated compounds, being the same as or different from each other, to said nanocomplexes obtained in step b).

23. Method for preparing the nanoassembled complexes according to claim 1 comprising at least the steps of:

a) preparing the self-assembled primary nucleus $NB_nAv_y$ by mixing avidin Av with the nucleic acid in stoichiometrically predefined molar ratios of nucleobases NB to avidin Av; and b) mixing the biotinylated surface protecting agent B-$X_a$-$PA_b$ with the primary nucleus $NB_nAv_y$ obtained in step a), the latter being added in stoichiometrically predefined molar ratios of avidin Av to the biotin B of B-$X_a$-$PA_b$; or a) preparing the conjugated compound $Av_y(B\text{-}X_a\text{-}PA_b)_z$ by mixing avidin Av with the surface protecting agent $B\text{-}X_a\text{-}PA_b$ in stoichiometrically predefined molar ratios of the biotin B of $B\text{-}X_a\text{-}PA_b$ to avidin Av; and b) mixing the conjugated compound $Av_y(B\text{-}X_a\text{-}PA_b)_z$ obtained in step a) with nucleic acid added in stoichiometrically predefined molar ratios of avidin Av to nucleobases NB;

wherein the mixing of nucleobases with avidin, free or conjugated, is carried out in salt-free aqueous solutions at a temperature from 0° C. to 50° C. and the stoichiometrically predefined molar ratios of nucleobases NB to avidin are in the range from 0.44 to 0.0001.

24. Method for preparing the nanoassembled complexes according to claim 23, wherein the stoichiometrically predefined molar ratios of nucleobases NB to avidin are in the range from 0.133 to 0.0044.

25. Method for preparing the nanoassembled complexes according to claim 23, wherein addition of the surface protecting agent $B\text{-}X_a\text{-}PA_b$ is carried out in aqueous solutions at a temperature from 0° to 50° C. and the stoichiometrically predefined molar ratios of avidin to $B\text{-}X_a\text{-}PA_b$ are comprised in the range from 4 to 0.02.

26. Method for preparing the nanoassembled complexes according to claim 23 comprising the additional step of preparing the biotinylated surface protecting agent $B\text{-}X_a\text{-}PA_b$.

27. Method for preparing the nanoassembled complexes according to claim 23 comprising the additional step of purifying the compound obtained in step a) or the nanoassembled complex obtained in step b) from monomeric avidin.

28. Method for preparing the nanoassembled complexes according to claim 23 comprising the additional step of further adding biotinylated compounds, being the same as or different from each other, to said nanocomplexes.

* * * * *